US00PP23838P2

(12) United States Plant Patent
Pineau

(10) Patent No.: US PP23,838 P2
(45) Date of Patent: Aug. 20, 2013

(54) ***FORSYTHIA* PLANT NAMED 'NIMBUS'**

(50) Latin Name: *Forsythia×intermedia*
Varietal Denomination: Nimbus

(75) Inventor: Patrick Pineau, Beaufort en Vallée (FR)

(73) Assignee: Pepinières Minier, Beaufort-en-Vallée (FR)

( * ) Notice: Subject to any disclaimer, the term of this patent is extended or adjusted under 35 U.S.C. 154(b) by 104 days.

(21) Appl. No.: 13/200,531

(22) Filed: Sep. 23, 2011

(51) Int. Cl.
*A01H 5/00* (2006.01)

(52) U.S. Cl.
USPC ..... Plt./230

(58) Field of Classification Search
USPC ..... Plt./230
See application file for complete search history.

*Primary Examiner* — Howard Locker
(74) *Attorney, Agent, or Firm* — C. A. Whealy

(57) ABSTRACT

A new and distinct cultivar of *Forsythia* plant named 'Nimbus', characterized by its compact, upright and outwardly spreading plant habit; vigorous growth habit; freely branching habit; dense and bushy growth habit; freely and continuous flowering habit; long flowering period; bright yellow-colored flowers; resistance to *Phytophthora*; and good garden performance.

2 Drawing Sheets

Botanical designation: *Forsythia×intermedia.*
Cultivar denomination: 'NIMBUS'.

BACKGROUND OF THE INVENTION

The present invention relates to a new and distinct cultivar of *Forsythia* plant, botanically known as *Forsythia×intermedia* and hereinafter referred to by the name 'Nimbus'.

The new *Forsythia* plant is a product of a planned breeding program conducted by the Inventor in La Ménitré, Maine et Loire, France. The objective of the breeding program was to develop new compact and freely flowering *Forsythia* plants.

The new *Forsythia* plant originated from an open-pollination in 2004 of *Forsythia×intermedia* 'Courdijau', disclosed in U.S. Plant Pat. No. 13,050, as the female, or seed, parent with an unknown selection of *Forsythia×intermedia* as the male, or pollen, parent. The new *Forsythia* plant was discovered and selected by the Inventor in 2006 as a single flowering plant within the progeny of the stated open-pollination in a controlled environment in La Ménitré, Maine et Loire, France.

Asexual reproduction of the new *Forsythia* plant by softwood cuttings in a controlled greenhouse environment in La Ménitré, Maine et Loire, France since May, 2006 has shown that the unique features of this new *Forsythia* plant are stable and reproduced true to type in successive generations of asexual reproduction.

SUMMARY OF THE INVENTION

Plants of the new *Forsythia* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Nimbus'. These characteristics in combination distinguish 'Nimbus' as a new and distinct *Forsythia* plant:

1. Compact, upright and outwardly spreading plant habit.
2. Vigorous growth habit.
3. Freely branching habit; dense and bushy growth habit.
4. Freely and continuous flowering habit.
5. Long flowering period.
6. Bright yellow-colored flowers.
7. Resistant to *Phytophthora.*
8. Good garden performance.

Plants of the new *Forsythia* can be compared to plants of the female parent, 'Courdijau'. In side-by-side comparisons, plants of the new *Forsythia* differ primarily from plants of 'Courdijau' in the following characteristics:

1. Plants of the new *Forsythia* are more compact than plants of 'Courdijau'.
2. Plants of the new *Forsythia* are more vigorous than plants of 'Courdijau'.
3. Plants of the new *Forsythia* are more freely branching than plants of 'Courdijau'.
4. Plants of the new *Forsythia* are more freely flowering than plants of 'Courdijau'.
5. Plants of the new *Forsythia* flower for a longer period of time than plants of 'Courdijau'.
6. Plants of the new *Forsythia* and 'Courdijau' differ in flower color.
7. Plants of the new *Forsythia* are more resistant to *Phytophthora* than plants of 'Courdijau'.

Plants of the new *Forsythia* can be compared to plants of *Forsythia×intermedia* 'Courtacour', not patented. In side-by-side comparisons, plants of the new *Forsythia* differed primarily from plants of 'Courtacour' in the following characteristics:

1. Plants of the new *Forsythia* were more erect than plants of 'Courtacour'.
2. Plants of the new *Forsythia* were more freely branching than plants of 'Courtacour'.
3. Plants of the new *Forsythia* were more freely flowering than plants of 'Courtacour'.
4. Plants of the new *Forsythia* flowered earlier than plants of 'Courtacour'.
5. Plants of the new *Forsythia* flowered longer than plants of 'Courtacour'.

6. Plants of the new *Forsythia* and 'Courtacour' differed in flower color.
7. Plants of the new *Forsythia* were more resistant to spring frost than plants of 'Courtacour'.

BRIEF DESCRIPTION OF THE PHOTOGRAPHS

The accompanying colored photographs illustrate the overall appearance of the new *Forsythia* plant showing the colors as true as it is reasonably possible to obtain in colored reproductions of this type. Colors in the photographs may differ slightly from the color values cited in the detailed botanical description which accurately describe the colors of the new *Forsythia* plant.

The photograph on the first sheet is a side perspective view of a typical plant of 'Nimbus' grown in a container.

The photograph on the second sheet is a close-up view of a typical flowering branch of 'Nimbus'.

DETAILED BOTANICAL DESCRIPTION

The aforementioned photographs and following observations, measurements and values describe plants grown in Grand Haven, Mich. during the spring and summer in an outdoor nursery and under conditions which closely approximate commercial *Forsythia* production. Plants were three years old when the photographs and the description were taken. In the description, color references are made to The Royal Horticultural Society Colour Chart, 2001 Edition, except where general terms of ordinary dictionary significance are used.

Botanical classification: *Forsythia×intermedia* 'Nimbus'.

Parentage:

*Female, or seed, parent.*—*Forsythia×intermedia* 'Courdijau', disclosed in U.S. Plant Pat. No. 13,050.

*Male, or pollen, parent.*—Unknown selection of *Forsythia×intermedia*, not patented.

Propagation:

*Type.*—By softwood cuttings.

*Time to initiate roots, summer.*—About 25 days at 16° C.

*Time to produce a rooted young plant, summer.*—About three months at 16° C.

*Root description.*—Fine; white in color.

*Rooting habit.*—Freely branching; dense.

Plant description:

*Plant form and growth habit.*—Perennial shrub; compact, upright and outwardly spreading plant habit; vigorous growth habit.

*Branching habit.*—Freely branching habit, dense and bushy growth habit, about 22 lateral branches develop per plant.

*Plant height.*—About 50 cm.

*Plant diameter* (*area of spread*).—About 50 cm.

Lateral branch description:

*Length.*—About 30 cm.

*Diameter.*—About 5 mm.

*Internode length.*—About 1 cm.

*Aspect.*—Upright to outwardly spreading.

*Texture, developing.*—Smooth, glabrous.

*Texture, developed.*—Woody.

*Color.*—Close to 152B.

Foliage description:

*Arrangement.*—Opposite, simple.

*Length.*—About 7.5 cm.

*Width.*—About 3 cm.

*Shape.*—Ovate to oblanceolate.

*Apex.*—Acute to acuminate.

*Base.*—Attenuate.

*Margin.*—Mostly entire with some slight indentations towards the apex.

*Texture, upper and lower surfaces.*—Smooth, glabrous.

*Venation pattern.*—Pinnate.

*Color.*—Developing leaves, upper surface: Close to 144A. Developing leaves, lower surface: Close to 143A. Fully expanded leaves, upper surface: Close to 141A; venation, close to 140A. Fully expanded leaves, lower surface: Close to 141A; venation, close to 140B.

*Petiole.*—Length: About 7 mm. Diameter: About 2 mm. Texture, upper and lower surfaces: Smooth, glabrous. Color, upper and lower surfaces: Close to 140A.

Flower description:

*Flower appearance/arrangement.*—Single star-shaped flowers; freely flowering habit with about two to 17 flowers per axillary node; flowers face upright and outwardly.

*Fragrance.*—None detected.

*Flower longevity.*—Flowers last for about three to six weeks on the plant and for about two to four weeks as a cut flower; flowers not persistent.

*Natural flowering season.*—Plants begin flowering in early May in Michigan.

*Flower diameter.*—About 3 cm.

*Flower depth.*—About 3 cm.

*Flower bud.*—Length: About 4 mm. Diameter: About 3 mm. Shape: Oblong. Color: Close to 146C.

*Petals.*—Arrangement/quantity: Single whorl of four petals fused at the base. Length: About 2.1 cm. Width: About 8 mm. Shape: Oblong. Apex: Obtuse. Margin: Entire; curled and undulate. Texture, upper and lower surfaces: Smooth, glabrous. Color: When opening, upper and lower surfaces: Close to 9A. Fully opened, upper and lower surfaces: Close to 6A; color does not fade with development.

*Sepals.*—Arrangement/quantity: Single whorl of four to five sepals fused at the base; calyx, star-shaped. Length: About 4 mm. Width: About 3 mm. Shape: Ovate. Apex: Acute. Margin: Entire. Texture, upper and lower surfaces: Smooth, glabrous. Color, upper and lower surfaces: Close to 146C.

*Peduncles.*—Length: About 3 mm. Diameter: About 1 mm. Strength: Strong. Texture: Smooth, glabrous. Angle: About 20° to 50° from vertical. Color: Close to 146C.

*Reproductive organs.*—Stamens: Quantity per flower: Two to four. Anther size: About 1 mm by 2 mm. Anther shape: Oblong. Anther color: Close to 6A. Pollen amount: Abundant. Pollen color: Close to 6A. Pistils: Quantity per flower: One. Pistil length: About 2 mm. Stigma shape: Rounded, two-lobed. Stigma color: Close to 145D. Style length: About 1 mm. Style color: Close to 145D. Ovary color: Close to 146C. Seeds and fruits: Seed and fruit development has not been observed on plants of the new *Forsythia.*

Garden performance: Plants of the new *Forsythia* have been observed to have good garden performance and to tolerate rain, wind and to tolerate temperatures ranging from about −28° C. to about 38° C.

Pathogen/pest resistance: Plants of the new *Forsythia* have been shown to be resistant to *Phytophthora*. Plants of the new *Forsythia* have not been shown to be resistant to pests and other pathogens common to *Forsythia* plants.

It is claimed:

1. A new and distinct *Forsythia* plant named 'Nimbus' as illustrated and described.

* * * * *

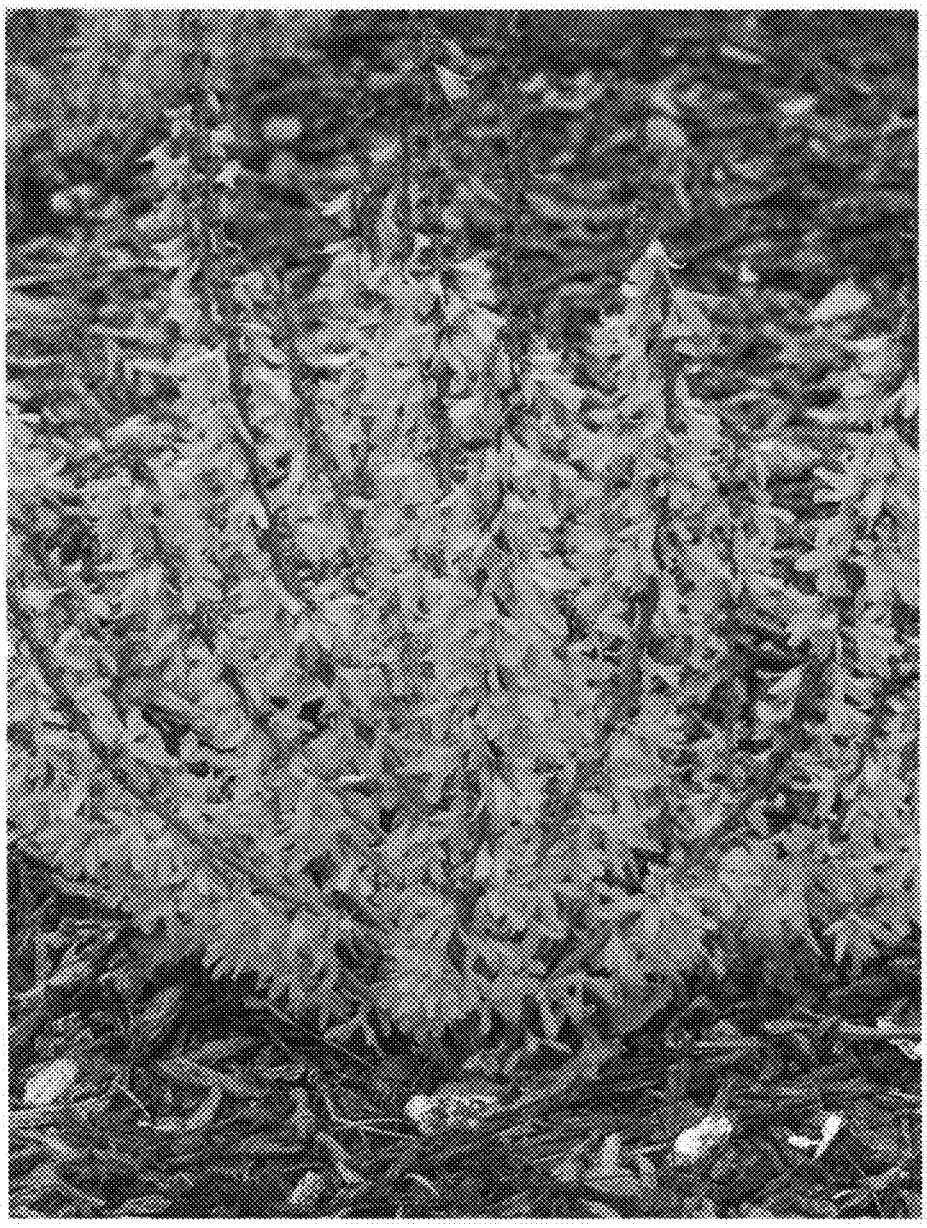

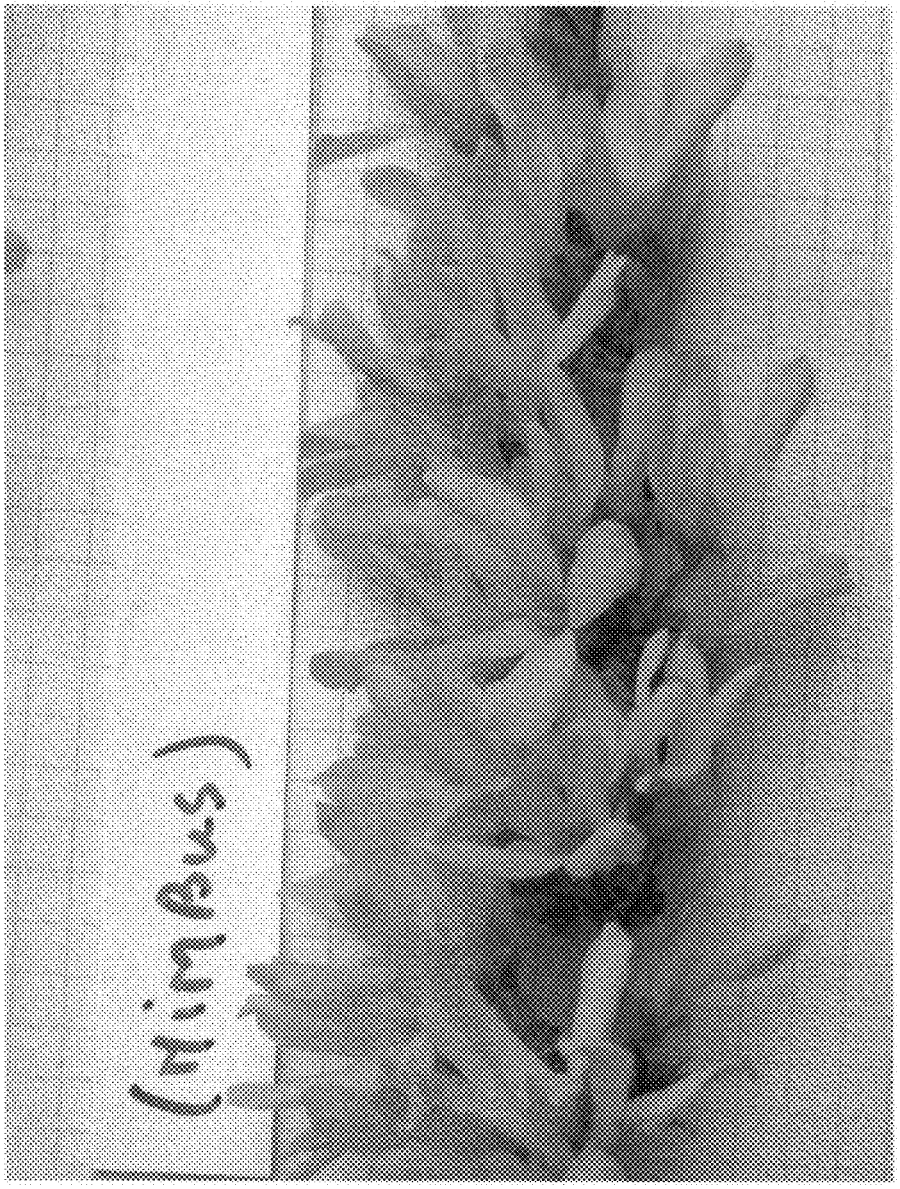
(Wimbus)